United States Patent [19]

Longest, Jr. et al.

[11] Patent Number: 5,353,357
[45] Date of Patent: Oct. 4, 1994

[54] METHODS AND APPARATUS FOR INSPECTING THE APPEARANCE OF SUBSTANTIALLY CIRCULAR OBJECTS

[75] Inventors: H. Cary Longest, Jr., Midlothian; Barry S. Smith, Hopewell, both of Va.

[73] Assignee: Philip Morris Incorporated, New York, N.Y.

[21] Appl. No.: 985,875

[22] Filed: Dec. 4, 1992

[51] Int. Cl.[5] .............................. G06K 9/00
[52] U.S. Cl. .............................. 382/8; 356/237; 348/92; 348/125
[58] Field of Search .................. 382/8; 358/106, 101; 356/237, 445; 250/223 R; 209/536

[56] References Cited

U.S. PATENT DOCUMENTS

| | | | |
|---|---|---|---|
| 3,818,223 | 6/1974 | Gibson et al. | 356/237 |
| 4,606,635 | 8/1986 | Miyazawa et al. | 358/106 |
| 4,969,746 | 11/1990 | McConnell et al. | 356/237 |
| 4,976,544 | 12/1990 | Neri | 356/237 |
| 5,127,737 | 7/1992 | Neri | 356/237 |

*Primary Examiner*—David K. Moore
*Assistant Examiner*—D. R. Anderson
*Attorney, Agent, or Firm*—Charles E. B. Glenn; James E. Schardt; Kevin B. Osborne

[57] ABSTRACT

Substantially circular objects such as the ends of the filters of filter tipped cigarettes are inspected to make sure they have an acceptable appearance. The object surface to be inspected is preferably cantilevered out from the object supporting structure, and any surface of the supporting structure which faces in the same direction as the object surface is preferably made visually contrasting with the object surface. The object surface is preferably illuminated obliquely and at an angle to the axis along which an image of the object is formed. The image is subjected to "blob" analysis to determine whether it has an acceptable appearance. Objects which do not have an acceptable appearance are rejected. A sophisticated user interface provides substantial information to an operator of the system.

33 Claims, 9 Drawing Sheets

METHODS AND APPARATUS FOR INSPECTING THE APPEARANCE OF SUBSTANTIALLY CIRCULAR OBJECTS

BACKGROUND OF THE INVENTION

This invention relates to methods and apparatus for inspecting the appearance of substantially circular objects such as the ends of cigarettes or cigarette components such as filters.

Modern manufacturing equipment is capable of producing products at very high speeds. For example, it is not at all uncommon for modern cigarette making equipment to produce cigarettes at the rate of 5000–6000 per minute, and speeds as high as 12,000 per minute are also achievable. It is, of course, desirable to inspect the appearance of products to the greatest possible extent. Abnormal appearance in itself may be a reason for rejecting a product. Moreover, abnormal appearance may indicate an underlying structural defect which may be another reason why the product should be rejected. In addition to facilitating rejection of defective products, appearance inspection may be used to identify the types of defects that are occurring so that the production equipment can be adjusted to reduce the occurrence of such defects.

In general, the more complete the inspection of products the better. This means, for example, that, if possible, the full image of each product should be inspected, rather than just inspecting portions of each image or inspecting only presumably representative sample product images. Also, the more current the results of the inspection the better. Thus it is generally preferable to inspect products as they are being made rather than later so that when defective products are detected, corrective action can be taken promptly to minimize the production of defective products.

The foregoing considerations become more critical as production speeds increase. It becomes both more important and more difficult to completely inspect all products made at high speeds because high speed equipment tends to be more sensitive and therefore more prone to producing defects if not maintained, operated, and adjusted properly. The need for immediate warning of defects is also more critical with high speed equipment because massive quantities of defective products can be produced in just a short time if defects are not detected promptly and the equipment either stopped or adjusted to eliminate the defects.

In the case of cigarettes, various types of defects can occur in the circular or substantially circular surfaces. (Although most cigarettes are intended to be circular, some cigarettes are intended to be oval. It will be readily apparent to those skilled in the art how the principles of this invention can be adapted to oval cigarettes. Thus, because oval objects are sufficiently like circular objects for present purposes, all such objects will be referred to herein as substantially circular.) Among the defects which can occur in the substantially circular surfaces of cigarettes are (1) absence of an intended component such as a filter, (2) improper size (i.e., too large or too small), (3) improper shape (e.g., not sufficiently circular), (4) improper sealing of a wrapper (e.g., a "flag" on the "plug wrap" (the paper wrapper around a filter component) or on the "tipping paper" (the wrapper which joins the filter to the tobacco rod)), (5) a gap between the plug wrap and the underlying filter material (a so-called "by-pass") or between the tipping paper and the underlying filter plug, or (6) discoloration of the filter surface (e.g., in the case of filters made with charcoal, one or more pieces of charcoal which have escaped from their intended location inside the filter to a visible surface of the filter (i.e., so-called "black eyes")).

In view of the foregoing, it is an object of this invention to provide methods and apparatus for inspecting the appearance of substantially circular objects such as the ends of cigarettes for one or more defects of the type described above.

It is another object of this invention to provide methods and apparatus for inspecting the appearance of substantially circular objects such as the ends of cigarettes at the extremely high speeds at which such articles are typically made in modern manufacturing equipment.

SUMMARY OF THE INVENTION

These and other objects of the invention are accomplished in accordance with the principles of the invention by forming a video image of each substantially circular object to be inspected. Preferably the substantially circular object is supported so that it visually contrasts with its background in the video image. In the case of inspection of the substantially circular end of a substantially cylindrical cigarette component, for example, the component may be supported so that the end to be inspected projects out from the supporting structure. The end of the component may then be illuminated obliquely so that little or no illumination falls on the adjacent portion of the supporting structure. The end of the component therefore tends to appear light or white against a dark or black background in the resulting video image. To further ensure contrast between the end of the component and the background, any structure such as the support structure which may appear in the video image is preferably made light absorbing (e.g., dark in color) and/or non-reflective.

The above-described video image is scanned out and digitized to produce a digital, grey scale image. Where the substantially circular object does not fill the entire field of view of the video image forming component (e.g., a video camera), only the portion of camera screen containing the object image is preferably scanned in order to increase the speed at which successive images can be captured. Alternatively or in addition, where the substantially circular object does not fill the entire field of view of the video camera, a "region of interest" containing all relevant image information may be defined. Only the image information in that region of interest may be digitized and/or subsequently processed.

The desired image information (e.g., that in the above-mentioned region of interest) which has been digitized is thresholded in order to binarize it so that pixels having grey scale values above a predetermined threshold value are assigned one of two values (e.g., binary 1) to indicate that they are relatively "white," while pixels having grey scale values below the threshold value are assigned the other of two values (e.g., binary 0) to indicate that they are relatively "black".

The binarized image data is then examined to identify all pixels which are at edges (i.e., transitions from black to white or vice versa) in the image. Edge pixels which are adjacent to one another are then associate with one another to define "blobs" in the image. The color of each blob (i.e., whether it is black or white) is then determined. Such parameters as the sizes and colors of the various blobs are then analyzed to determine whether or not the substantially circular object has an acceptable appearance. For example, assuming that the substantially circular object is white against a black background, and further assuming that the substantially circular object is the largest component of the image, then the image should contain one relatively large white blob. Moreover, the perimeter of this relatively large white blob should be a certain size. If it is too small, the substantially circular object may be rejected as too small. If it is too large, the substantially circular object may be rejected as being too large, as having a flag, or as not having the desired substantially circular shape (i.e., because the perimeter of a crushed circle is greater than the perimeter of the circle prior to crushing). Such defects as black eyes and by-passes are indicated by black blobs within the above-mentioned large white blob. If a black blob of at least a predetermined minimum size is detected, the substantially circular object may also be rejected as having an unacceptable appearance.

The methods and apparatus of this invention preferably include separating substantially circular objects found to have an unacceptable appearance from those having an acceptable appearance. The invention also preferably includes providing the operator with current information regarding the number and/or rate of defects being found, and may also include a visual display of the objects being inspected, with special emphasis on those found to be defective.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
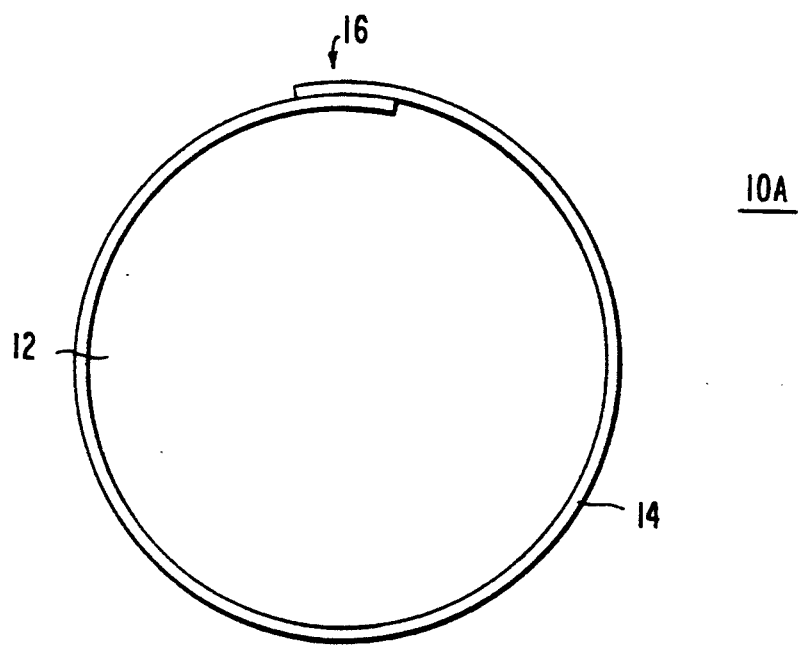
FIG. 1 is a simplified end view of the filter on a filter tipped cigarette, the appearance of which is to be inspected in accordance with the principles of this invention.

A typical substantially circular object 10A to be inspected in accordance with this invention is shown in FIG. 1. Although the object shown in FIG. 1 is the filter end of a filter-tipped cigarette, it will be understood that the invention is equally applicable to inspecting the appearance of other substantially circular objects. For example, object 10A could be just a cigarette filter plug prior to attachment to a tobacco rod. The object shown in FIG. 1 is typical of objects having an acceptable appearance in the illustrative application of the invention described herein. In particular, object 10A has a large, white, central region 12 which is the end of the bundle of cellulose acetate fibers which perform the cigarette smoke filtering function. This bundle of fibers is surrounded by one or more layers of paper 14 which help to hold the bundle of fibers together, give the bundle a smooth outer surface, and/or attach the filter to the tobacco rod of the cigarette. (Although more than one layer of paper may be present in an actual product, only one representative layer 14 is shown in FIG. 1.) Each paper layer such as 14 is typically applied by being wrapped or formed around the underlying structure so that portions of the paper overlap one another and can be glued together at side seam 16. Although the boundary between fiber bundle 12 and paper layer 14 is clearly depicted in FIG. 1, that boundary may not be as clearly visible in an actual product. The same is true of the overlapping paper layers in seam 16.

Figure 2:
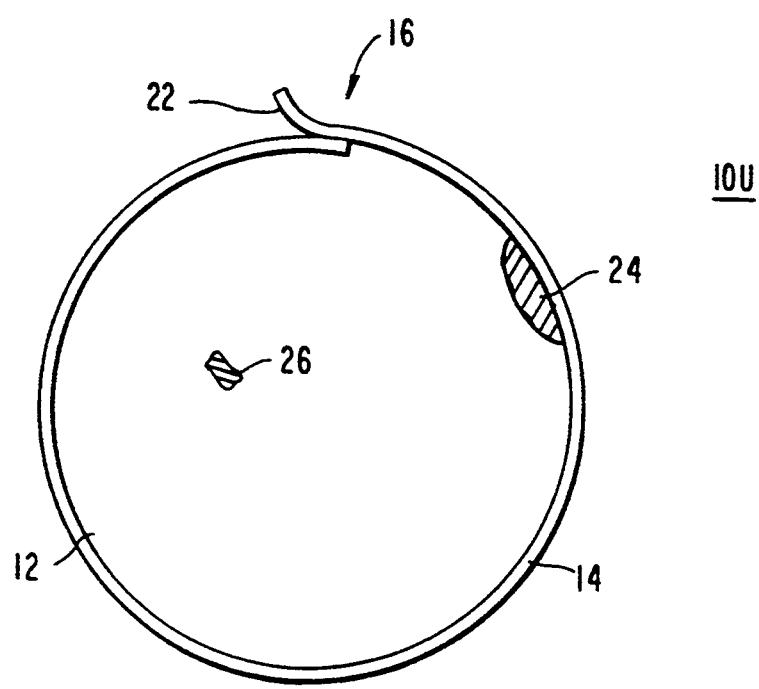
FIG. 2 is a view similar to FIG. 1 showing the end of a cigarette filter having several representative defects in appearance.

FIG. 2 shows another substantially circular object 10U which is generally similar to object 10A but which has several representative defects in its appearance, any one of which renders the appearance of the object unacceptable. One of the defects in the appearance of object 10U is that side seam 16 is not properly glued down, leaving a so-called "flag" 22 of paper sticking out from one side of the object. Such flags may be caused by any of several malfunctions of the cigarette making machinery such as an under-sized or over-sized fiber bundle 12, insufficient glue being applied to seam 16, a snag in the machinery which lifts and may curl or fold back a portion of the paper 14 in the seam. Whatever the cause, flag 22 renders the product unsatisfactory or unacceptable to the consumer, and so it is important to reject all production having this defect and to promptly remedy the cause of the defect. Accordingly, this is one type of defect which the present invention is able to detect.

Another typical defect in the appearance of object 10U is a gap 24 between fiber bundle 12 and paper 14. Such a gap (called a "by-pass" because it may allow some smoke to pass around fiber bundle 12 without being fully filtered) may be due to a fiber bundle which is improperly shaped or too small, a paper layer 14 which has not been fully pressed against the underlying fiber bundle, or some other similar problem in the cigarette or filter manufacturing equipment. A by-pass such as by-pass 24 tends to show up as a relatively dark region, especially when objects 10 are illuminated obliquely in accordance with this invention as described in detail below.

Still another typical defect in the appearance of object 10U is a discolored region 26 on the surface of fiber bundle 12. Discolored region 26 may be due to any of several reasons such as staining of a portion of fiber bundle 12 or, in the case of filters which include charcoal particles sandwiched between two axially spaced plugs of cellulose acetate, a bit of charcoal which has escaped from its intended location inside the filter structure. The latter type of discolored region is known as a "black eye," but for convenience herein, all discolored regions on fiber bundle 12 will sometimes be referred to as black eyes.

Figure 3:
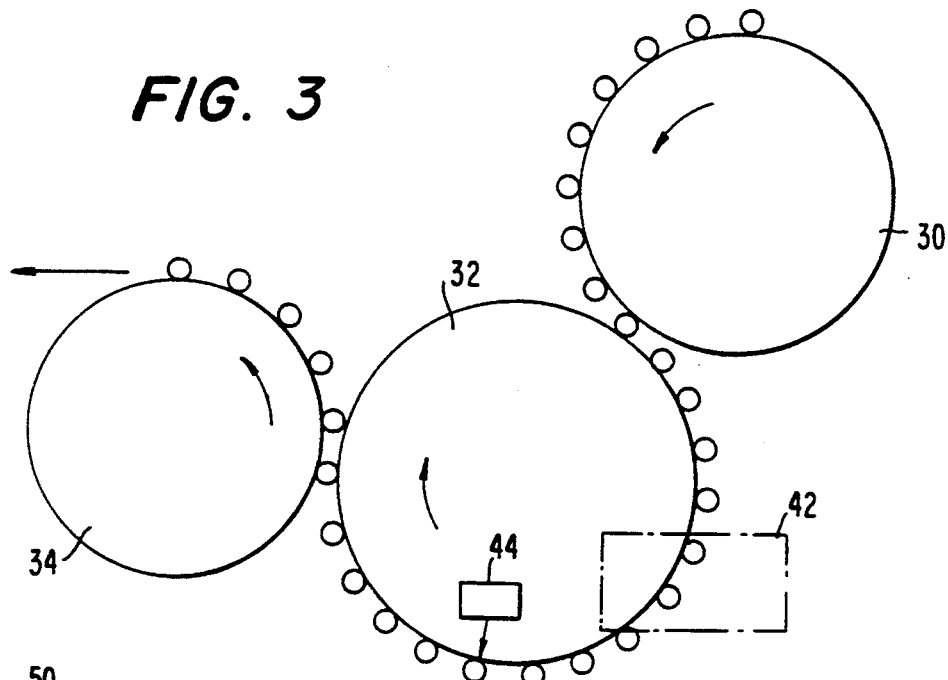
FIG. 3 is a simplified elevational view of a portion of illustrative cigarette making machinery showing how the appearance inspection apparatus of this invention can be added.
Figure 4:
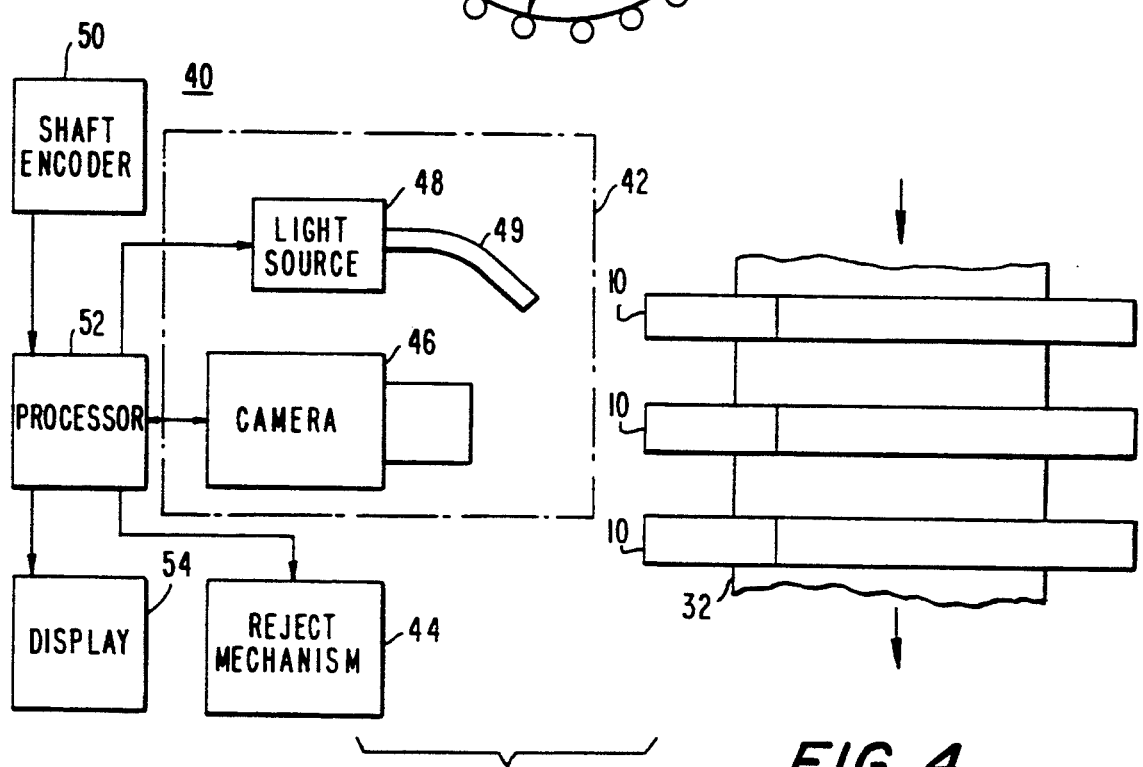
FIG. 4 is a schematic block diagram of illustrative appearance inspection apparatus constructed in accordance with this invention.

Although the appearance inspection apparatus 40 of this invention can be set up to operate at any convenient location in the apparatus which produces or otherwise handles the substantially circular objects to be inspected, FIG. 3 illustrates one possible location of the image-capturing portion 42 of this apparatus in conventional filter tipped cigarette manufacturing equipment (see also FIG. 4). In particular, in a conventional Max S model tipper available from Hauni-Werke Korber & Co. KG of Hamburg, Germany, fully finished filter-tipped cigarettes 10 are conveyed one after another, side by side on the cylindrical surface of conventional Hauni inspection drum 30. As drum 30 rotates, the Hauni apparatus performs conventional inspection operations on the cigarettes on that drum. The cigarettes are then passed to the conventional Hauni rejection drum 32. The Hauni apparatus rejects any cigarette it has found to be defective by blowing it off drum 32. Cigarettes which have not been rejected continue on to exit drum 34, which conveys the cigarettes out of the tipper (e.g., by passing them to a conventional tray filler or a mass flow conveyor system (not shown)).

It has been found convenient to locate the image-capturing portion 42 of the apparatus of this invention adjacent a relatively upstream portion of rejection drum 32. The reject output of the present apparatus can then be used as an additional input to the conventional Hauni reject mechanism, or a separate reject mechanism 44 can be added to rejection drum 32 at a relatively downstream location.

Whatever the location at which substantially circular objects 10 are imaged in accordance with this invention, objects 10 are preferably well-differentiated from their background in the resulting image information. A particularly good way to achieve this is shown in FIG. 4 and includes cantilevering the ends of cigarettes 10 to be inspected out from the adjacent end of drum 32 on which the cigarettes are being conveyed as they are imaged by camera 46. To further help differentiate objects 10 from their background, the end of drum 32 adjacent to camera 46 is preferably made relatively dark and non-reflective, and the surfaces of objects 10 to be inspected are obliquely illuminated by light from light source 48. In particular, fiber optic bundle 49 directs light from light source 48 so that it has an angle of incidence of approximately 45° on the end of the cigarette 10 which is directly opposite camera 46 and which is therefore being imaged by the camera. The axis along which camera 46 images cigarette 10 is substantially perpendicular to the plane of the end of the cigarette being imaged. Cantilevering and obliquely lighting the end of the cigarette tends to cause any light from fiber optic bundle 49 which does not fall on the end of the cigarette to fall on portions of drum 32 which are spaced from the cigarette in the resulting image. Making any surfaces of drum 32 which are adjacent to the cigarette in the resulting image dark and non-reflective also helps ensure good contrast between the cigarette and its background in the image.

Although drum 32 rotates continuously, light source 48 may briefly illuminate or "strobe" each time the end of a cigarette 10 is directly opposite camera 46. This has the effect of effectively stopping or "freezing" the motion of the cigarette being imaged so that camera 46 forms a still or nearly still image of the cigarette. The image-capturing and image-processing apparatus 40 of this invention is synchronized to the motion of cigarettes 10 through apparatus such as drums 30, 32, and 34 by a shaft encoder 50 which produces an output signal pulse each time the drum apparatus has moved by a predetermined amount. This enables processor 52 to know exactly when a cigarette 10 is directly opposite camera 46. Processor 52 then strobes light source 48 and begins the process of reading out or "grabbing" the cigarette image captured by camera 46.

In order to save time in the image grabbing operation in applications in which the significant image information does not fill the entire field of view of camera 46, the camera is preferably positioned so that the significant image information is in the portion of the field of view which is scanned first when an image is grabbed from the camera. In addition, the scanning is stopped as soon as the portion of the field of view containing the significant image information has been scanned. This principle is illustrated by FIG. 5.

Figure 5:
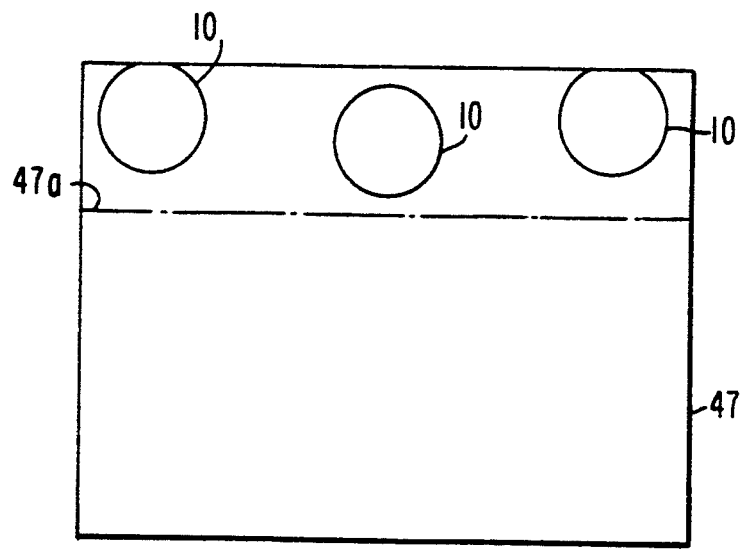
FIG. 5 is a simplified depiction of a typical image captured by the video camera in the apparatus of FIG. 4.

As shown in FIG. 5, the typical field of view 47 of camera 46 is 640 pixels wide by 480 pixels high. Camera 46 is typically scanned horizontally from top to bottom. Accordingly, camera 46 is placed relative to the objects to be imaged so that the significant image information is at the top of the field of view of the camera. In particular, in imaging the ends of cigarettes 10, an image of a good size is contained within an area less than about 150 by 150 pixels in field of view 47. Processor 52 is therefore set up to scan camera 46 down only until 150 vertical pixels have been scanned, i.e., scanning stops when line 47a is reached. (Although only the central cigarette image 10 in FIG. 5 is of interest, field of view 47 may include portions of adjacent cigarettes on drum 32. It will be explained shortly how this extraneous image information is eliminated from consideration.) By scanning only a portion of the field of view of camera 46 each time an image is to be captured, the rate at which the apparatus can capture and process images is substantially increased.

Figure 6A:
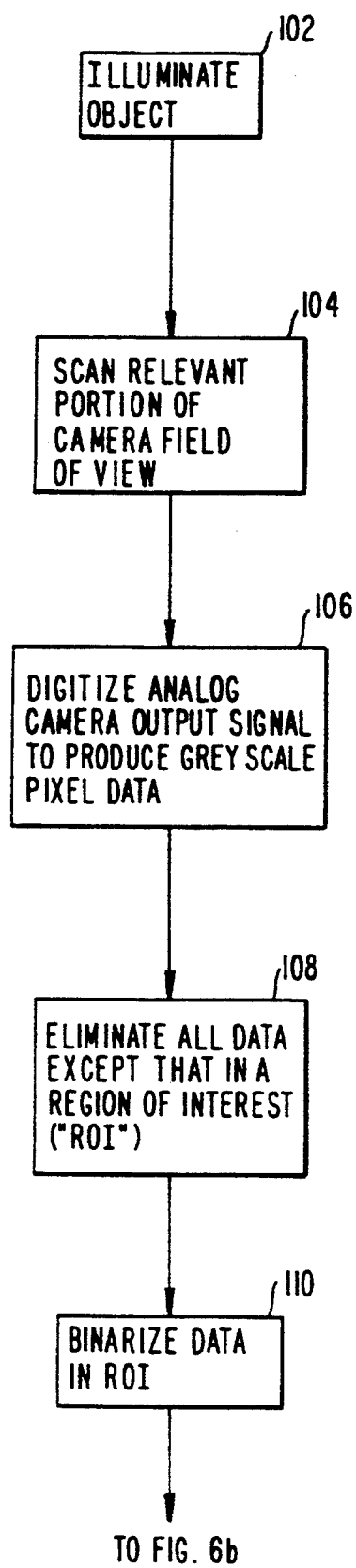
FIGS. 6a and 6b (referred to collectively as FIG. 6) are a flow chart showing illustrative appearance inspection steps which may be carried out by the apparatus of FIG. 4 in accordance with this invention.
Figure 6B:
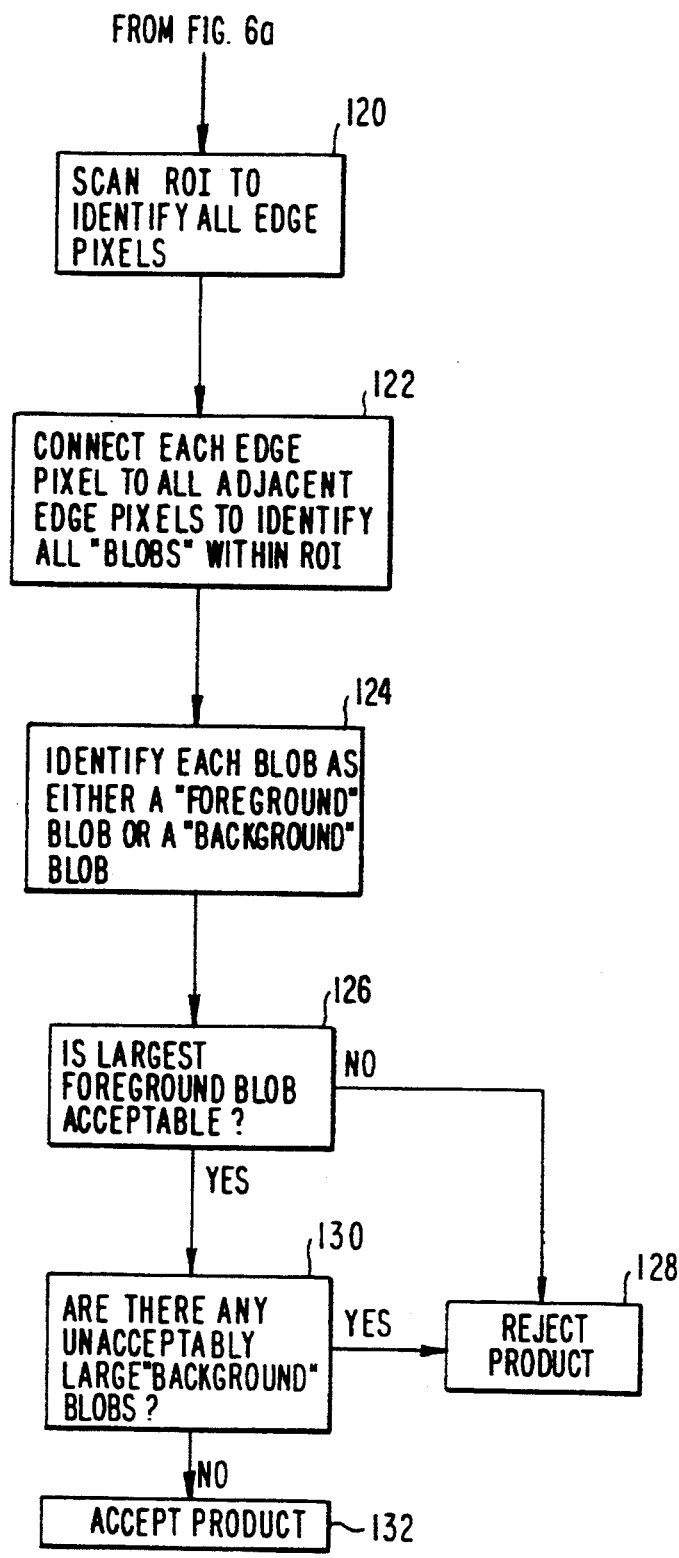

FIG. 6 shows steps which may be performed by apparatus 40 in order to perform an appearance inspection operation in accordance with this invention. Most of these steps are carried out or at least controlled by processor 52 which may be a programmable, general purpose digital computer such as a conventional Intel Model 386 or 486 microprocessor or compatible backplane into which conventional frame grabber and image grabber boards (such as those available from Pattern Processing Technologies, Inc. of Eden Prairie, Minn.) can be plugged.

In step 102, processor 52 causes light source 48 to briefly illuminate the end of a cigarette 10 which is directly opposite camera 46. As mentioned above, the signal from shaft encoder 50 enables processor 52 to know when a cigarette is thus properly positioned opposite camera 46 and therefore when the processor should begin an inspection cycle by illuminating the cigarette.

In step 104 processor 52 scans the relevant portion of the field of view of camera 46 (e.g., as described above in connection with FIG. 5). Thus, for example, processor 52 may only scan out the portion of the field of view 47 of camera 46 down to line 47a. The output signal of camera 46 is typically an analog signal.

In step 106 processor 52 digitizes the analog output signal of camera 46 to produce digital grey scale pixel data representative of the analog output signal. In this digital data each pixel is represented by a digital value (e.g., from 0 to 255) indicative of the brightness of the corresponding portion of the image received by camera 46. Assuming that the field of view of camera 46 is 640 pixels wide, and that line 47a is 150 pixels below the top of the camera screen, the grey scale image data will cover an area 640 pixels wide by 150 pixels high.

Figure 7:
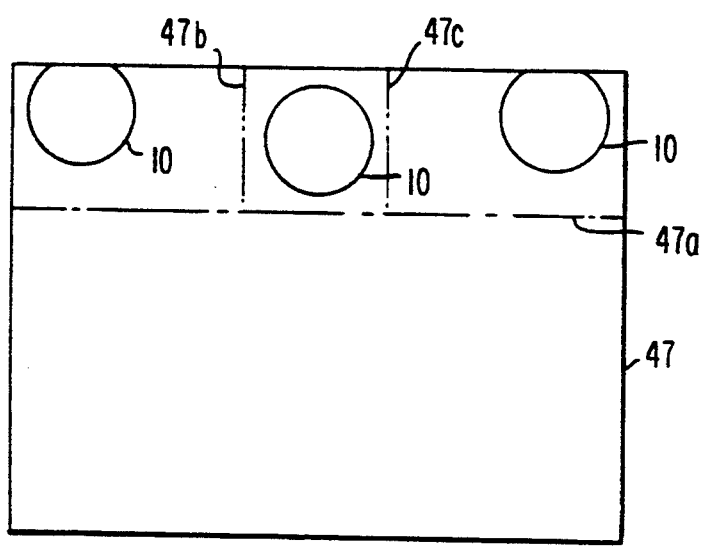
FIG. 7 is a view similar to FIG. 5 showing how the image may be restricted to a particular region of interest in accordance with this invention.

Assuming that the significant image information is contained in only a portion of the above-mentioned area, processor 52 performs step 108 to limit further processing of the image data to just the portion of the image area containing significant information. In the illustrative embodiment being described the significant image information is within the 150 pixels in the horizontal center of the field of view of camera 46. Accordingly, as is illustrated by FIG. 7, in step 108 processor 52 limits all further consideration of the digital image data to the data between vertical lines 47b (245 pixels to the right of the left-hand edge of field of view 47) and 47c (245 pixels to the left of the right-hand edge of field of view 47). The area bounded by the top of field of view 47 and by lines 47a-c is referred to in subsequent steps as the "region of interest" or "ROI."

Figure 8:
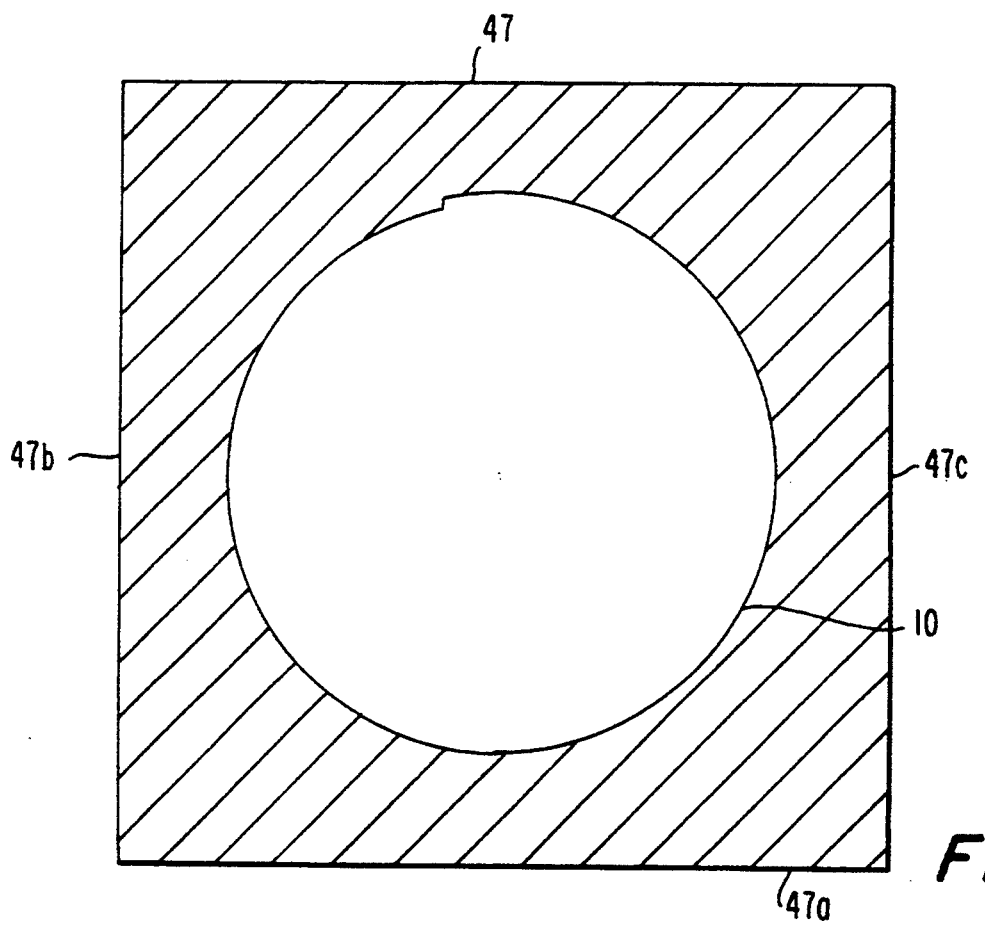
FIG. 8 is a simplified depiction of typical image data during processing in accordance with the method steps of FIG. 6.

In step 110 the digital grey scale image data for each pixel in the ROI is compared to a threshold value which is selected to give good separation between relatively light pixels and relatively dark pixels. For example, this threshold value is preferably chosen so that all pixels associated with the background around the white or relatively light cigarette end 10 in the ROI will have values on one side of the threshold value, while all pixels making up the image of cigarette end 10 (assuming that it is of acceptable appearance) will have values on the other side of this threshold value. Assuming, for example, that relatively light pixels have values above the threshold value, those pixels are assigned one of two "binary" values (e.g., 1) for further processing. All other pixels are assigned the other of two "binary" values (e.g., 0). (Although the traditional binary values 0 and 1 are mentioned above, it will be understood that any other two values (e.g., −1 and 1) can be used instead (and are embraced by the term binary as used herein) to respectively identify pixels having grey scale values above or below the threshold value used to differentiate "light" pixels from "dark" pixels.) It will be appreciated that the techniques mentioned above (e.g., the oblique lighting from fiber optic bundle 49, the cantilevering of the cigarette ends from drum 32, and the darkening of the surface of drum 32 opposite camera 46) all help to ensure that it is easy for processor 52 (in step 110) to separate relatively light cigarette end 10 from a relatively dark surrounding "background." FIG. 8 shows how the image of a "good" cigarette 10 may appear in the ROI after performance of step 110. In FIG. 8 the dark background pixel region is shown shaded, while the light "foreground" pixel region is shown unshaded.

In step 120 processor 52 scans the ROI to identify all "edge" pixels (i.e., pixels which are at transitions between light and dark image regions). For example, this can be done by starting with the top row of pixels and scanning the rows one after another from left to right. Each row will start out dark, but after the first few all-dark rows, rows will be encountered in which the first pixels are dark but then there is a pixel which is light. That first light pixel is identified as an edge pixel. Scanning will then continue through successive white pixels until the next pixel is dark again. Then the immediately preceding light pixel can be identified as another edge pixel. This scanning process continues until the entire ROI has been scanned and all edge pixels have been identified.

Figure 9:
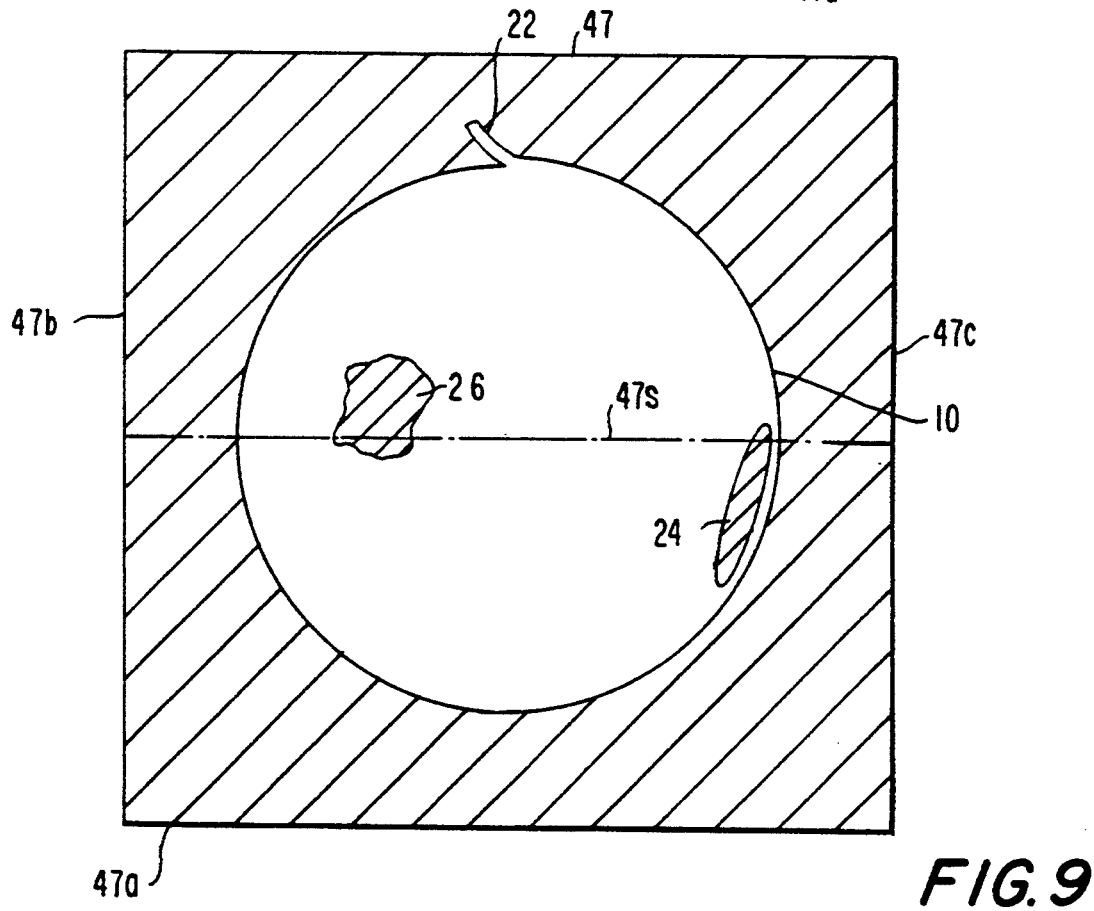
FIG. 9 is similar to FIG. 8 and shows other typical image data.

FIG. 9 is similar to FIG. 8 but shows a cigarette having several defects of the type shown in FIG. 2 and described above. The threshold level discussed above in connection with step 110 is preferably chosen to make defects such as by-pass 24 and black eye 26 appear as dark regions like the background region surrounding the end of the cigarette. It will be appreciated that when the image of FIG. 9 is scanned for edge pixels in step 120, many more such pixels will be encountered than are encountered in scanning the good cigarette image shown in FIG. 8. In particular, there will be extra edge pixels associated with flag 22, by-pass 24, and black eye 26. For example, in scanning from left to right along line 47s, there will first be several dark pixels. Then a first light pixel associated with the perimeter of cigarette 10 will be encountered and identified as an edge pixel. After that, several light pixels are encountered until the edge of black eye 26 is reached, at which point the last light pixel is identified as an edge pixel. Black eye 26 is traversed as a succession of dark pixels until a first light pixel to the right of the black eye is encountered. This is identified as another edge pixel. More light pixels follow until the left-hand edge of by-pass 24 is encountered, at which point the last light pixel is identified as an edge pixel. By-pass 24 is then traversed as a succession of dark pixels until the first light pixel associated with the wrapper around the cellulose acetate fiber bundle is encountered. This first light pixel is identified as another edge pixel, and the last light pixel just before entering the right-hand dark background region is identified as still another edge pixel. Accordingly, instead of identifying only two edge pixels as would be the case in scanning along line 47s in a good image like that shown in FIG. 8, six edge pixels are identified in scanning along line 47s in FIG. 9.

Figure 10:
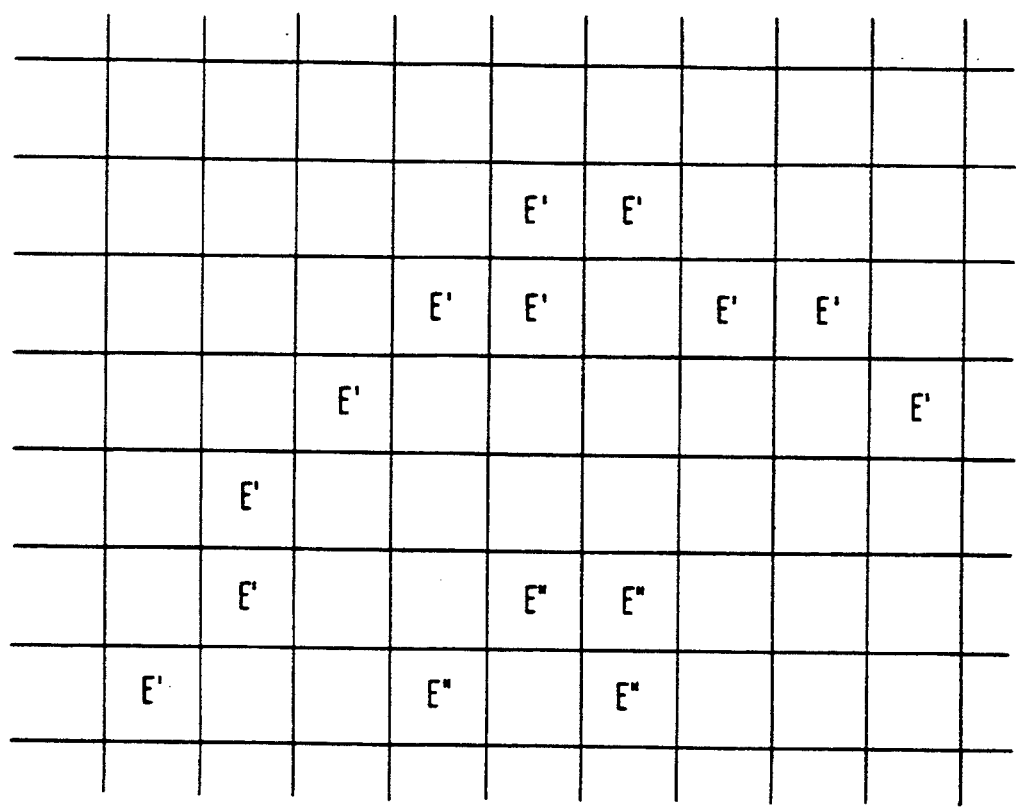
FIG. 10 is a simplified depiction of a typical region of pixels in image data of the type shown in FIGS. 8 and 9, with certain pixels identified by reference characters as having certain attributes.

In step 122 each edge pixel is connected to as many adjacent edge pixels as possible. In FIG. 10, wherein each square represents one pixel, and wherein all edge pixels are identified by the letter E, all $E^1$ edge pixels are considered to be adjacent to one another and are identified as one group of adjacent edge pixels. Similarly, all $E''$ edge pixels are considered to be adjacent to one another and are identified as another group of adjacent edge pixels. Assuming that the significant image information is always completely surrounded by a dark background region, all groups of edge pixels identified in step 122 will be closed shapes. Each of these closed shapes is referred to as a "blob." In FIG. 8, for example, there is only one large light blob. All edge pixels identified in connection with the image of FIG. 8 are associated with the periphery of that one large light blob. In FIG. 9, on the other hand, there is one large light blob containing two smaller dark blobs 24 and 26. Computer programs for performing this and subsequent blob identification and analysis is available from Pattern Processing Technologies, Inc. (mentioned above), and is part of PPT's 400 VPC Vision Program Manager Software.

In step 124 each blob identified in step 122 is examined to determine whether it is a light "foreground" blob or a dark "background" blob. This can be done, for example, by determining whether a single pixel inside the blob which is not also part of another blob is light or dark. If the pixel tested is light, then the blob is a light "foreground" blob. If the pixel tested is dark, then the blob is a dark "background" blob.

In step 126 the foreground blob having the largest number of associated edge pixels is tested for acceptability. For example, it may be known that the large light foregoing blob in FIG. 8 should have 480 to 530 edge pixels. If there is no foreground blob with this number of edge pixels, the image should be rejected (step 128) as having an unacceptable appearance. If cellulose acetate fiber bundle 12 is significantly under-sized or over-sized, the largest foreground blob will have fewer than 480 or more than 530 edge pixels. Similarly, flag 22 (FIG. 9) will increase the number of edge pixels of the largest foreground blob beyond the acceptable upper limit. If the cigarette is not substantially circular, that will also increase the number of edge pixels of the largest foreground blob beyond the acceptable upper limit. Thus, comparing the number of edge pixels associated with the largest foreground blob enables the apparatus to identify any of several possible defects in the image. If in step 126 the largest foreground blob is not found to have a number of edge pixels within a predetermined acceptable range, control passes to step 128 so that the associated product 10 can be rejected when it reaches rejection mechanism 44 (FIGS. 3 and 4). On the other hand, if the image passes the step 126 test, then control passes to step 130 where the image is further tested for acceptability.

In step 130 the image data is tested for any unacceptably large background blobs. For example, it may be predetermined that any background blob having more than a certain number of edge pixels (e.g., nine or more) renders the associated image unacceptable. Accordingly, in step 130, the number of edge pixels associated with each background blob is compared to this predetermined limit, and if any background blob is found to have more than the threshold number of edge pixels, control passes to step 128 to cause the associated product to be rejected. On the other hand, if the image has no excessively large background blob, control passes to step 132 to allow the associated product to be accepted.

Figure 11:
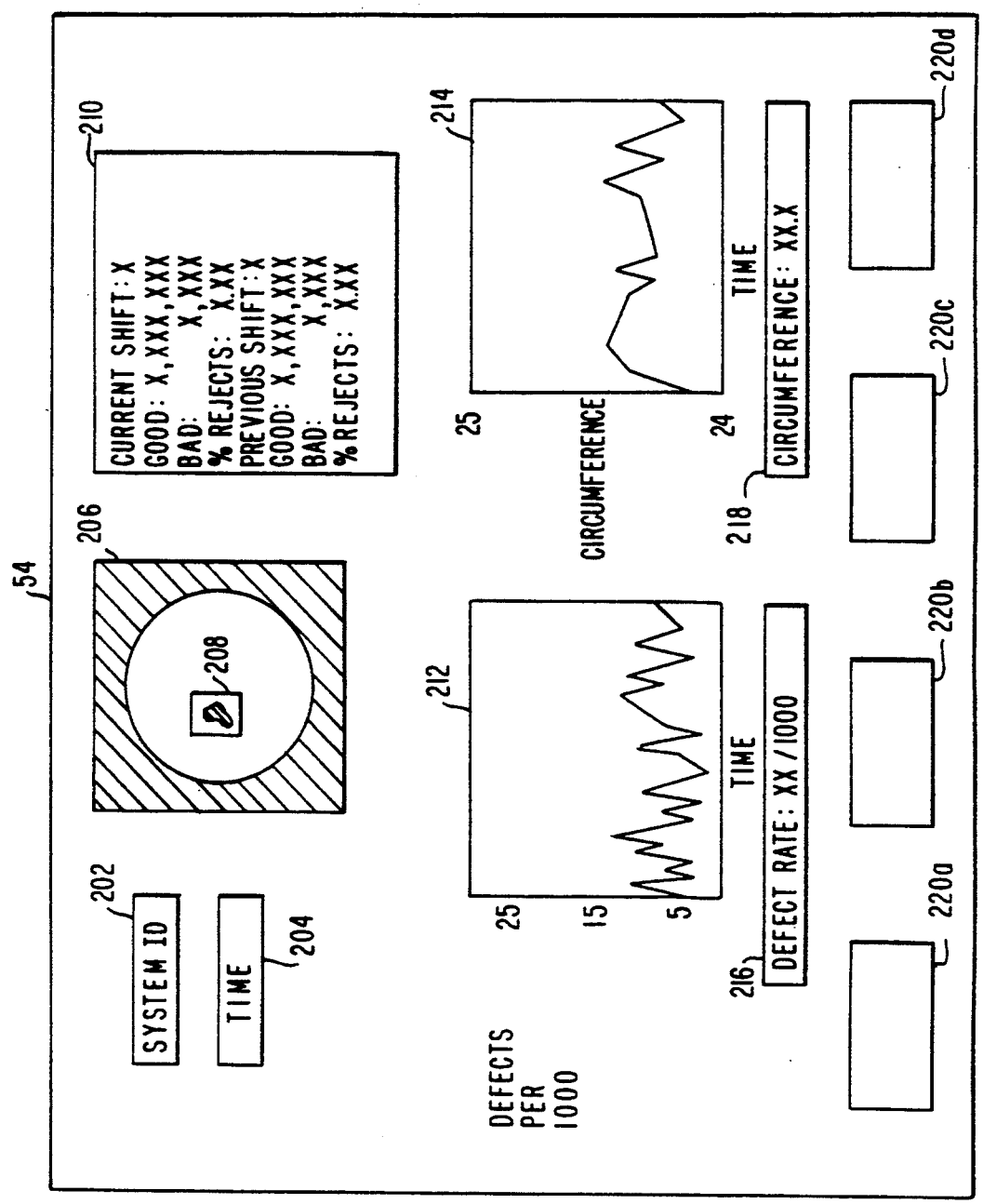
FIG. 11 is a simplified view of information of the kind which may appear on a computer display viewable by the operator of the system in accordance with this invention.

As has been mentioned, it can be important or at least helpful to provide the operator of the system with current information as to the results of the appearance inspection operation. This may be done, for example, via the computer display screen 54 of apparatus 40 (see again FIG. 4). FIG. 11 shows a typical display on screen 54. This display is, of course, controlled by processor 52. Display 54 may include information areas or fields as follows:

1. Field 202: An identification of the cigarette making machine with which the appearance inspection system is being used.
2. Field 204: The current time of day.
3. Field 206: The current digital grey scale image of the region of interest in the field of view of camera 46. Preferably, when an image is identified as defective, that image is held longer than normal (e.g., for three seconds) to give the operator of the system more time to examine it. In addition, a rectangular box 208 is drawn around the portion of the image which caused it to be rejected.
4. Field 210: A table containing cumulative data for the current shift of operation of the inspection apparatus, and similar data for the preceding shift of operation. For each shift the data includes (a) a shift identifier, (b) the number of good cigarettes produced, (c) the number of bad cigarettes detected and rejected, and (d) the percent of total production rejected.
5. Field 212: A moving graph or histogram showing recent experience of the system in terms of number of rejects per 1000 cigarettes produced.
6. Field 214: A moving graph or histogram showing recent experience of the system in terms of cigarette circumference measured.
7. Field 216: The most recent experience of the system in terms of number of rejects per 1000 cigarettes produced.
8. Field 218: The most recent experience of the system in terms of cigarette circumference measured.
9. Fields 220a-d: Several "buttons" which can be used by the operator of the system (assuming that display 54 is a "touch screen") to control various functions of the system. For example, one or more of buttons 220 can be used to tell the system about a shift change. Another button 220 can be used to reset the counters in processor 52 which are used to accumulate the data shown in field 210 for the current shift.

Figure 12:
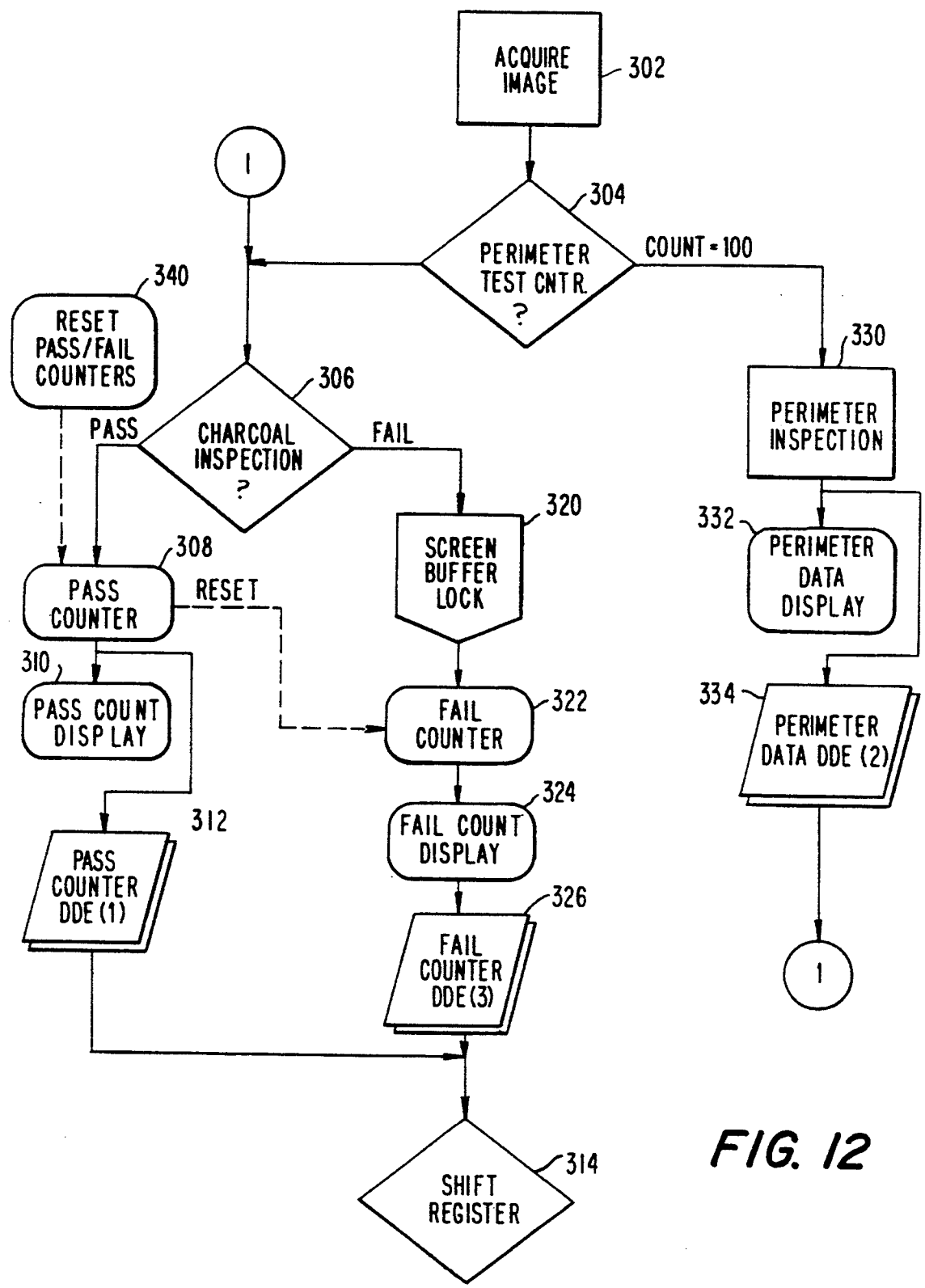
FIG. 12 is a flow chart showing alternative and/or additional appearance inspection steps which may be carried out by the apparatus of FIG. 4 in accordance with this invention.

FIG. 12 is a flow chart of operations which can be preformed by processor 52 to inspect cigarettes as described above and to support display 54 as shown in FIG. 11. In step 302 the system acquires the next image to be inspected. This step can be performed as shown in more detail in step 102–124 in FIG. 6. Assuming that the perimeter or circumference of every cigarette is not to be measured, then in step 304 a perimeter test counter is incremented. The steps to the right of step 304 are then performed only each time the perimeter test counter reaches a predetermined number (e.g., 100). The steps to the left of step 304 are performed for every cigarette.

In step 306 a so-called "charcoal inspection" is performed. This is the test for unacceptably large background blobs which is step 130 in FIG. 6. Although referred to as charcoal inspection in FIG. 12, any sufficiently large black eye or by-pass will cause the associated image to fail this inspection step.

If the image passes inspection step 306, control passes to step 308 in which a pass counter in processor 52 is incremented.

In step 310 the associated portion of field 210 on display 54 is updated to reflect the new data in the pass counter.

In step 312 the new pass counter data is passed via an associated, conventional, dynamic data exchange ("DDE") to conventional computer programs which produce the graph in field 212 on display 54. These computer programs may also produce the data shown in field 216.

In step 314 appropriate data indicating that the cigarette just inspected has passed inspection is entered into a shift register in processor 52. The shift register associated with step 314 (sometimes referred to as shift register 314) is shifted at the same rate that images are acquired in step 302. Data is entered into an upstream stage of the shift register. A downstream stage of the shift register is used as an output signal to control reject mechanism 44 (FIGS. 3 and 4). The number of shift register stages between the upstream stage and the downstream stage corresponds to the time required for a cigarette to travel from the location at which its image is acquired in step 302 to the location at which it is rejected, if necessary, by reject mechanism 44. When step 314 is reached from step 312, the data entered into the shift register is that which will subsequently cause reject mechanism 44 to allow the cigarette to pass and not be rejected.

If the cigarette fails the inspection test of step 306, then control passes from step 306 to step 320. In step 320 processor locks the image displayed in field 206 for a predetermined time interval (e.g. three seconds), and also augments that image with an appropriate rectangle 208 around the background blob which caused the image to fail test 306.

In test 322 a fail counter in processor 52 is incremented, and in step 324 the new fail counter data is used to update the appropriate portion of field 210 on display 54.

Step 326 is similar to above-described step 312 and involves passing the new fail counter data to the above-mentioned computer programs which produce the graph in field 212 and the data in field 216 on display 54.

When step 314 is performed after performance of step 326, the data entered in shift register 314 is that which will cause the cigarette having the defective image to be rejected when that cigarette reaches reject mechanism 44.

Although the perimeter inspection of step 330 could be performed for every cigarette (as in step 126 in FIG. 6), in the embodiment shown in FIG. 12 that inspection is only performed on every 100th cigarette. Accordingly, when a 100th cigarette is detected, perimeter inspection test 330 is performed on the image data as described above in connection with step 126. In particular, the number of edge pixels associated with the largest foreground blob in converted to a perimeter measurement by multiplying the number of edge pixels by a predetermined scale factor.

In step 332 the perimeter data in field 218 on display 54 is updated.

In step 334 the new perimeter data is passed to conventional computer programs which produce the graph in field 214 in a manner similar to above-described steps 312 and 326. Control then passes from step 334 to step 306 so that charcoal inspection can be performed on the cigarette which has just been used to provide updated perimeter data.

Step 340 is performed whenever it is desired to reset the pass counter associated with step 308 and the fail counter associated with step 322. For example, step 340 may be performed whenever there is a shift change.

It will be understood that the foregoing is merely illustrative of the principles of the invention, and that various modifications can be made by those skilled in the art without departing from the scope and spirit of the invention. For example, the particular information shown on display 54 can be varied as desired.

The invention claimed is:

1. Apparatus for determining whether an end surface of a cigarette has an acceptable appearance, said apparatus comprising:

means for forming an image of said end surface against a contrasting background;

means for digitizing said image as a plurality of pixels, each of said pixels having an initial digital value indicative of the brightness of a corresponding portion of said image;

means for processing said pixels so that each pixel having an initial digital value which has a first polarity relative to a predetermined threshold value is assigned a first of two processed digital values, and so that all other pixels are assigned a second of said two processed digital values, said threshold values being selected so that said background and substantially discolored area of said end surface are assigned said first processed digital value and substantially undiscolored areas of said end surface are assigned said second processed digital value;

means for identifying as edge pixels those pixels which are adjacent to transitions between pixels having said first and second processed digital values;

means for associating edge pixels which are adjacent to one another so as to identify a boundary of each blob in said image;

means for identifying each blob as a first type of blob or a second type of blob by determining whether each boundary surrounds pixels having said first processed digital value or said second processed digital value, respectively;

means for calculating a characteristic of any blob of at least one of said blob types; and means for determining acceptability of said image by comparing said calculated characteristic to a predetermined value.

2. The apparatus defined in claim 1 wherein said means for determining acceptability includes: means for comparing said calculated characteristic of any blob of said first blob type to a first predetermined value; and means for comparing said calculated characteristic of any blob of said second blob type to a second predetermined value.

3. The apparatus defined in claim 2 wherein said means for calculating a characteristic includes means for calculating a size of any blob of said second type and said means for determining acceptability further comprises:

means for determining whether the largest of said calculated size of any blobs of said second type approximately equals a predetermined size.

4. The apparatus defined in claim 3 wherein said means for calculating a characteristic includes means for calculating a size of any blob of said first type.

5. The apparatus defined in claim 4 further comprising:

means for rejecting said cigarette if said means for determining acceptability determines that said image is an unacceptable image.

6. The apparatus defined in claim 1 further comprising:

means for supporting said cigarette during operation of said means for forming an image so that said end surface is spaced from said means for supporting.

7. The apparatus defined in claim 6 wherein said means for supporting comprises a drum on which said cigarette is supported with its longitudinal axis substantially parallel to the longitudinal axis of said drum.

8. The apparatus defined in claim 6 further comprising:
means for illuminating said end surface so that any light from said means for illuminating which falls on said means for supporting is spaced from said end surface in the image formed by said means for forming an image.

9. The apparatus defined in claim 8 wherein said means for forming an image forms said image along a first predetermined axis, and wherein said means for illuminating illuminates said end surface along a second predetermined axis which is inclined relative to said first predetermined axis.

10. The apparatus defined in claim 9 wherein said second predetermined axis is inclined relative to said first predetermined axis by an angle of approximately 45°.

11. The apparatus defined in claim 9 wherein said first predetermined axis is substantially perpendicular to said end surface.

12. The apparatus defined in claim 9 wherein said second predetermined axis is oblique to said end surface.

13. The apparatus defined in claim 8 wherein said means for supporting has a surface adjacent to said cigarette which faces in substantially the same direction as said end surface, and wherein said surface of said means for supporting is made so that it visually contrasts with said end surface.

14. The apparatus defined in claim 13 wherein surfaces of said means for supporting on which light may fall from said means for illuminating are made substantially non-reflective.

15. The apparatus defined in claim 13 wherein surfaces of said means for supporting on which light may fall from said means for illuminating are made substantially light-absorbing.

16. The apparatus defined in claim 6 wherein said means for supporting moves said cigarette relative to said means for forming an image, and wherein said apparatus further comprises:
means for momentarily illuminating said end surface so that said means for forming an image forms a substantially still image of said end surface.

17. The apparatus defined in claim 16 wherein said means for momentarily illuminating comprises:
means for synchronizing the illumination of said end surface with the motion of said means for supporting so that said end surface is illuminated when said end surface is at a predetermined location in the field of view of said means for forming an image.

18. The apparatus defined in claim 1 wherein said cigarette is one of a succession of substantially similar objects, wherein said apparatus substantially similarly operates on all of said cigarettes one after another in succession, and wherein said apparatus further comprises:
means for displaying the image of a cigarette which is formed by said means for forming an image; and
means for prolonging the display of the image of a cigarette which has been determined to have an unacceptable appearance by said means for determining whether at least one of said boundaries has a predetermined characteristic so that an operator of the apparatus has additional time to view that image.

19. A method for determining whether an end surface of a cigarette has an acceptable appearance, said method comprising the steps of:
forming an image of said end surface against the contrasting background;
digitizing said image as a plurality of pixels, each of said pixels having an initial digital value indicative of the brightness of a corresponding portion of said image;
processing said pixels so that each pixel having an initial digital value which has a first polarity relative to a predetermined threshold value is assigned a first of two processed digital values, and so that all other pixels are assigned a second of said two processed digital values, said threshold values being selected so that said background and substantially discolored areas of said end surface are assigned said first processed digital value and substantially undiscolored areas of said end surface are assigned said second processed digital value;
identifying as edge pixels those pixels which are adjacent to transitions between pixels having said first and second processed digital values;
associating edge pixels which are adjacent to one another so as to identify a boundary of each blob in said image;
identifying each blob as a first type of blob or a second type of blob by determining whether each boundary surrounds pixels having said first processed digital value or said second processed digital value, respectively;
calculating a characteristic of any blob of at least one of said blob types; and
determining acceptability of said image by comparing said calculated characteristic to a predetermined value.

20. The method defined in claim 19 wherein said acceptability determining step includes: comparing said calculated characteristic of any blob of said first blob type to a first predetermined value; and comparing said calculated characteristic of any blob of said second blob type to a second predetermined value.

21. The method defined in claim 20 wherein said step of calculating a characteristic includes calculating a size of any blob of said second type and said step of determining acceptability further comprises the step of:
determining whether the largest of said calculated size of any blob of said second type approximately equals a predetermined size.

22. The method defined in claim 21 wherein said step of calculating a characteristic includes calculating a size of any blob of said first type.

23. The method defined in claim 20 further comprising the step of:
rejecting said cigarette if said step of determining acceptability determines that said image is an unacceptable image.

24. The method defined in claim 20 further comprising the step of:
supporting said cigarette with a support structure during said step of forming an image so that said end surface of said cigarette is spaced from said support structure.

25. The method defined in claim 24 further comprising the step of:
illuminating said end surface from a light source so that any light from said light source which falls on said support structure is spaced from said end surface in the image formed in said step of forming an image.

26. The method defined in claim 25 wherein said image is formed along a first predetermined axis in said step of forming an image, and wherein in said step of illuminating said end surface said end surface is illuminated along a second predetermined axis which is inclined relative to said first predetermined axis.

27. The method defined in claim 26 wherein said second predetermined axis is inclined relative to said first predetermined axis by an angle of approximately 45°.

28. The method defined in claim 26 wherein said first predetermined axis is substantially perpendicular to said end surface.

29. The method defined in claim 26 wherein said second predetermined axis is oblique to said end surface.

30. The method defined in claim 24 wherein said support structure has a surface adjacent to said cigarette which faces in substantially the same direction as said end surface, and wherein said surface of said support structure is made so that it visually contrasts with said end surface.

31. The method defined in claim 24 wherein said support structure moves said cigarette relative to said light source, and wherein said method further comprises the step of:
  momentarily illuminating said end surface so that a substantially still image of said end surface is formed during said step of forming an image.

32. The method defined in claim 31 wherein said step of momentarily illuminating comprises the step of:
  synchronizing the illumination of said end surface with the motion of said support structure.

33. The method defined in claim 20 wherein said cigarette if one of a succession of substantially similar objects, wherein said method substantially similarly operates on all of said cigarettes one after another in succession, and wherein said method further comprises the steps of:
  displaying the image of a cigarette which is formed in said step of forming an image; and
  prolonging the display of the image of a cigarette which has been determined to have an unacceptable appearance in said step of determining acceptability so that an operator of the apparatus has additional time to view that image.

* * * * *